United States Patent
Weihe

(10) Patent No.: US 10,226,269 B2
(45) Date of Patent: Mar. 12, 2019

(54) SURGICAL FORCEPS

(71) Applicant: COVIDIEN LP, Mansfield, MA (US)

(72) Inventor: Jason G. Weihe, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 371 days.

(21) Appl. No.: 14/722,468

(22) Filed: May 27, 2015

(65) Prior Publication Data

US 2016/0345991 A1    Dec. 1, 2016

(51) Int. Cl.
*A61B 17/28* (2006.01)
*A61B 17/29* (2006.01)
*A61B 18/14* (2006.01)

(52) U.S. Cl.
CPC ...... *A61B 17/29* (2013.01); *A61B 2017/2937* (2013.01); *A61B 2017/2944* (2013.01); *A61B 2018/145* (2013.01)

(58) Field of Classification Search
CPC ............ A61B 17/29; A61B 2017/2937; A61B 2017/2944; A61B 2018/145
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument" ; Innovations That Work, Jun. 2003. (4 pages).

(Continued)

*Primary Examiner* — Tigist Demie

(57) ABSTRACT

A forceps includes an end effector assembly having first and second jaw members, each including a proximal flange and a distal jaw body defining a tissue-treating surface. The second jaw member is both proximally offset and spaced-apart from the first jaw member. One or more resilient bands extends between and interconnects the proximal flanges of the jaw members. The resilient band(s) is configured to bias the first and second jaw members towards an open position. The resilient band(s) is configured to flex in response to distal translation of the second jaw member relative to the first jaw member to thereby move the second jaw member relative to the first jaw member to a closed position for grasping tissue between the tissue-treating surfaces thereof. In the closed position, the second jaw member is disposed in an aligned orientation and is approximated relative to the first jaw member.

8 Claims, 4 Drawing Sheets

(56) References Cited

U.S. PATENT DOCUMENTS

| | | |
|---|---|---|
| D358,887 S | 5/1995 | Feinberg |
| D384,413 S | 9/1997 | Zlock et al. |
| 5,709,680 A | 1/1998 | Yates et al. |
| H1745 H | 8/1998 | Paraschac |
| D402,028 S | 12/1998 | Grimm et al. |
| D408,018 S | 4/1999 | McNaughton |
| 5,922,002 A | 7/1999 | Yoon |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,554,829 B2 | 4/2003 | Schulze et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,935,052 B2 | 5/2011 | Dumbauld |
| 7,951,150 B2 | 5/2011 | Johnson et al. |
| 8,038,956 B2 | 10/2011 | Li |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| 8,317,787 B2 | 11/2012 | Hanna |
| D680,220 S | 4/2013 | Rachlin |
| 8,491,625 B2 | 7/2013 | Horner |
| 8,568,444 B2 | 10/2013 | Cunningham |
| 8,636,761 B2 | 1/2014 | Cunningham et al. |
| 9,084,608 B2 | 7/2015 | Larson et al. |
| 9,211,657 B2 | 12/2015 | Ackley et al. |
| 9,375,256 B2 | 6/2016 | Cunningham et al. |
| 9,375,262 B2 | 6/2016 | Reschke et al. |
| 9,439,717 B2 | 9/2016 | Orszulak et al. |
| 9,445,865 B2 | 9/2016 | Sartor et al. |
| 9,456,863 B2 | 10/2016 | Moua |
| 9,468,453 B2 | 10/2016 | Hart et al. |
| 9,474,570 B2 | 10/2016 | McKenna et al. |
| 9,492,225 B2 | 11/2016 | Dycus et al. |
| 9,539,053 B2 | 1/2017 | Hixson et al. |
| 9,554,841 B2 | 1/2017 | Guerra et al. |
| 9,554,845 B2 | 1/2017 | Arts |
| 9,579,117 B2 | 2/2017 | Kappus et al. |
| 9,579,146 B2 | 2/2017 | Johnson et al. |
| 9,585,716 B2 | 3/2017 | Johnson et al. |
| 9,622,810 B2 | 4/2017 | Hart et al. |
| 9,642,671 B2 | 5/2017 | Lee et al. |
| 9,655,673 B2 | 5/2017 | McCullough, Jr. et al. |
| 9,713,491 B2 | 7/2017 | Roy et al. |
| 9,717,548 B2 | 8/2017 | Couture |
| 9,770,288 B2 | 9/2017 | Gilbert |
| 9,795,402 B2 | 10/2017 | Allen, IV et al. |
| 9,877,775 B2 | 1/2018 | Hart |
| 9,943,357 B2 | 4/2018 | Cunningham et al. |
| 10,070,916 B2 | 9/2018 | Artale |
| 2004/0254607 A1 * | 12/2004 | Wittenberger ..... A61B 17/2812 606/205 |
| 2007/0299387 A1 * | 12/2007 | Williams ............... A61B 17/29 604/22 |
| 2009/0306541 A1 | 12/2009 | Kano et al. |
| 2010/0094286 A1 | 4/2010 | Chojin |
| 2010/0286691 A1 | 11/2010 | Kerr et al. |
| 2011/0251609 A1 | 10/2011 | Johnson et al. |
| 2011/0295314 A1 | 12/2011 | Staud |
| 2013/0066230 A1 | 3/2013 | Li et al. |
| 2013/0085516 A1 | 4/2013 | Kerr et al. |
| 2013/0190753 A1 | 7/2013 | Garrison et al. |
| 2013/0289562 A1 | 10/2013 | Skarda et al. |
| 2013/0304115 A1 * | 11/2013 | Miyamoto ......... A61B 17/2909 606/205 |
| 2014/0221994 A1 | 8/2014 | Reschke |
| 2014/0236149 A1 | 8/2014 | Kharin et al. |
| 2014/0243887 A1 | 8/2014 | Kim et al. |
| 2014/0250686 A1 | 9/2014 | Hempstead et al. |
| 2014/0353188 A1 | 12/2014 | Reschke et al. |
| 2015/0018816 A1 | 1/2015 | Latimer |
| 2015/0032106 A1 | 1/2015 | Rachlin |
| 2015/0051640 A1 | 2/2015 | Twomey et al. |
| 2015/0057702 A1 | 2/2015 | Edmondson et al. |
| 2015/0066026 A1 | 3/2015 | Hart et al. |
| 2015/0088122 A1 | 3/2015 | Jensen |
| 2015/0088126 A1 | 3/2015 | Duffin et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |

(56) References Cited

FOREIGN PATENT DOCUMENTS

| | | |
|---|---|---|
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).

(56) References Cited

OTHER PUBLICATIONS

Dulemba et al. "Use of a Bipolar Electrothermal Vessel Sealer in Laparoscopically Assisted Vaginal Hysterectomy" Sales/Product Literature; Jan. 2004. (1 page).

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000. (1 page).

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000. (4 pages).

Levy et al. "Use of a New Energy-based Vessel Ligation Device During Vaginal Hysterectomy" Int'l Federation of Gynecology and Obstetrics (FIGO) World Congress 1999. (1 page).

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000. (1 page).

Jarrett et al., "Use of the LigaSure Vessel Sealing System for Peri-Hilar Vessels in Laparoscopic Nephrectomy" Sales/Product Literature 2000. (1 page).

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.. (1 page).

McLellan et al. "Vessel Sealing for Hemostasis During Gynecologic Surgery" Sales/Product Literature 1999. (1 page).

Heniford et al. "Initial Research and Clinical Results with an Electrothermal Bipolar Vessel Sealer" Oct. 1999 (1 page).

\* cited by examiner

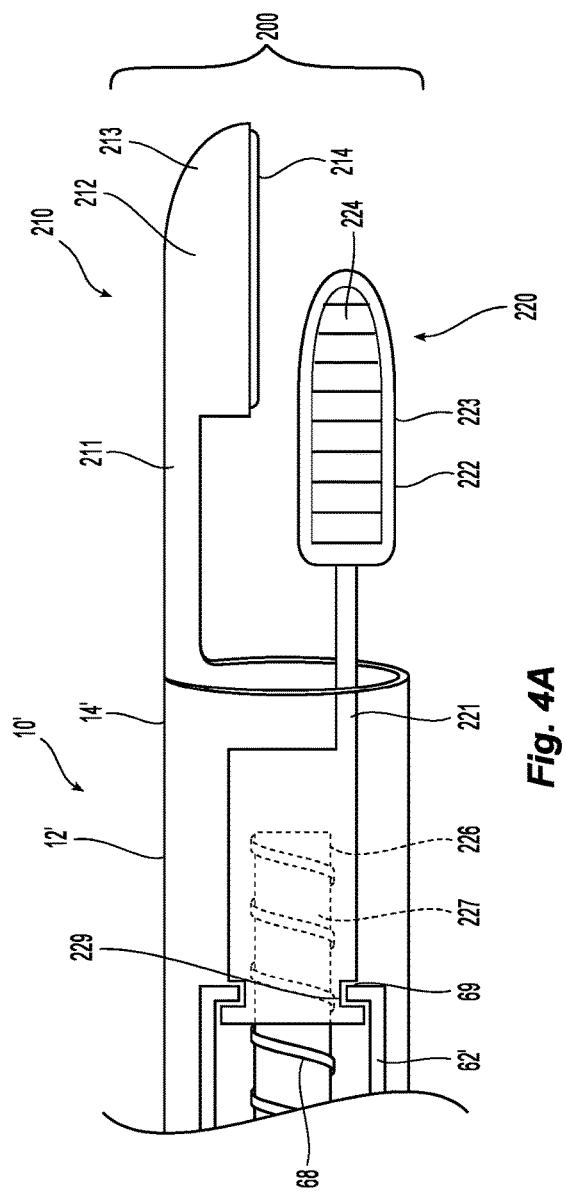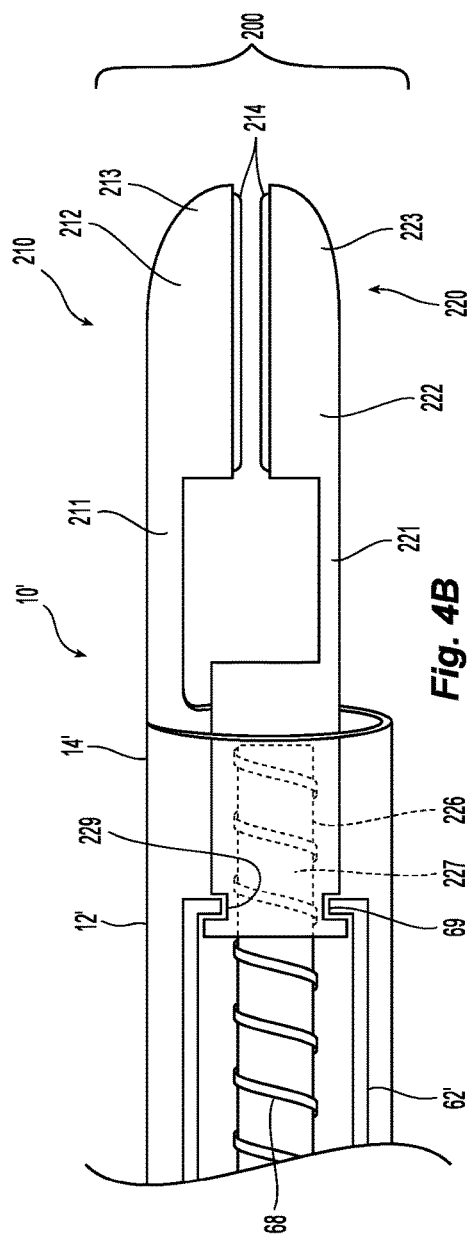

SURGICAL FORCEPS

BACKGROUND

Technical Field

The present disclosure relates to surgical instruments and, more particularly, to surgical forceps configured for grasping and treating tissue.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

Generally, surgical instruments, including surgical forceps, can be classified as disposable instruments, e.g., instruments that are discarded after a single use, or reusable instruments, e.g., instruments capable of being sterilized for repeated use. As can be appreciated, those instruments that are configured for single-use must be cost-efficient while still being capable of effectively performing their intended functions.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A forceps provided in accordance with aspects of the present disclosure includes an end effector assembly having first and second jaw members. Each of the first and second jaw members includes a proximal flange and a distal jaw body defining a tissue-treating surface. The second jaw member is both proximally offset and spaced-apart from the first jaw member. One or more resilient bands extends between and interconnects the proximal flanges of the first and second jaw members. The one or more resilient bands is configured to bias the first and second jaw members towards an open position. The one or more resilient bands is further configured to flex in response to distal translation of the second jaw member relative to the first jaw member to thereby move the second jaw member relative to the first jaw member to a closed position for grasping tissue between the tissue-treating surfaces thereof. The second jaw member is disposed in an aligned orientation and is approximated relative to the first jaw member in the closed position.

In an aspect of the present disclosure, the one or more resilient bands includes one or more spring steel bands.

In another aspect of the present disclosure, the one or more resilient bands includes first and second legs engaged with the respective proximal flanges of the first and second jaw members and a body interconnecting the first and second legs. Further, in the open position, interior angles defined between the legs and the body of the one or more resilient bands may be at a minimum, while such angles may be at a maximum in the closed position.

In still another aspect of the present disclosure, the forceps further includes a shaft having the proximal flange of the first jaw member engaged thereto and a drive bar slidably disposed within the shaft. The drive bar includes the proximal flange of the second jaw member engaged thereto.

In yet another aspect of the present disclosure, distal translation of the drive bar through and relative to the shaft moves the second jaw member from the open position to the closed position to grasp tissue between the tissue-treating surfaces of the first and second jaw members.

In still yet another aspect of the present disclosure, a handle assembly is operably associated with the drive bar and includes a movable handle selectively actuatable for translating the drive bar through and relative to the shaft.

In another aspect of the present disclosure, one or both of the tissue-treating surfaces is adapted to connect to a source of energy for treating tissue grasped between the tissue-treating surfaces of the first and second jaw members.

Another forceps provided in accordance with aspects of the present disclosure includes an end effector assembly having first and second jaw members each including a proximal flange and a distal jaw body defining a tissue-treating surface. The first and second jaw members are movable between an open position, wherein the second jaw member is longitudinally offset, spaced-apart, and rotationally offset relative to the first jaw member, and a closed position, wherein the second jaw member is longitudinally aligned, approximated, and rotationally aligned relative to the first jaw member. The tissue-treating surfaces of the first and second jaw members cooperate to grasp tissue therebetween in the closed position.

In an aspect of the present disclosure, the forceps further includes a shaft having the proximal flange of the first jaw member engaged thereto and a drive bar slidably disposed within the shaft. The drive bar is operably engaged with the proximal flange of the second jaw member and may be configured such that distal translation of the drive bar through and relative to the shaft moves the second jaw member from the open position to the closed position to grasp tissue between the tissue-treating surfaces of the first and second jaw members.

In another aspect of the present disclosure, a handle assembly is operably associated with the drive bar. The handle assembly includes a movable handle selectively actuatable for translating the drive bar distally through and relative to the shaft.

In yet another aspect of the present disclosure, a lead screw is disposed within and fixed relative to the shaft and a nut is operably disposed about the lead screw and engaged with the proximal flange of the second jaw member. The drive bar is rotatably coupled to the nut such that translation of the drive bar through and relative to the shaft translates the second jaw member relative to the lead screw and rotates the second jaw member relative to the lead screw.

In still another aspect of the present disclosure, the second jaw member is rotatable about a rotation axis that is parallel to or coaxial with a longitudinal axis of the shaft.

In still yet another aspect of the present disclosure, at least one of the tissue-treating surfaces is adapted to connect to a source of energy for treating tissue grasped between the tissue-treating surfaces of the first and second jaw members.

BRIEF DESCRIPTION OF THE DRAWINGS

Various aspects and features of the present disclosure described herein with reference to the drawings wherein:

FIG. 4A is an enlarged, side, perspective view of the distal end of another forceps provided in accordance with the present disclosure, wherein jaw members of the end effector assembly of the forceps are disposed in an open position; and FIG. 4B is an enlarged, side, perspective view of the distal end of the forceps of FIG. 4A, wherein the jaw members of the end effector assembly of the forceps are disposed in a closed position.

DETAILED DESCRIPTION

Figure 1:
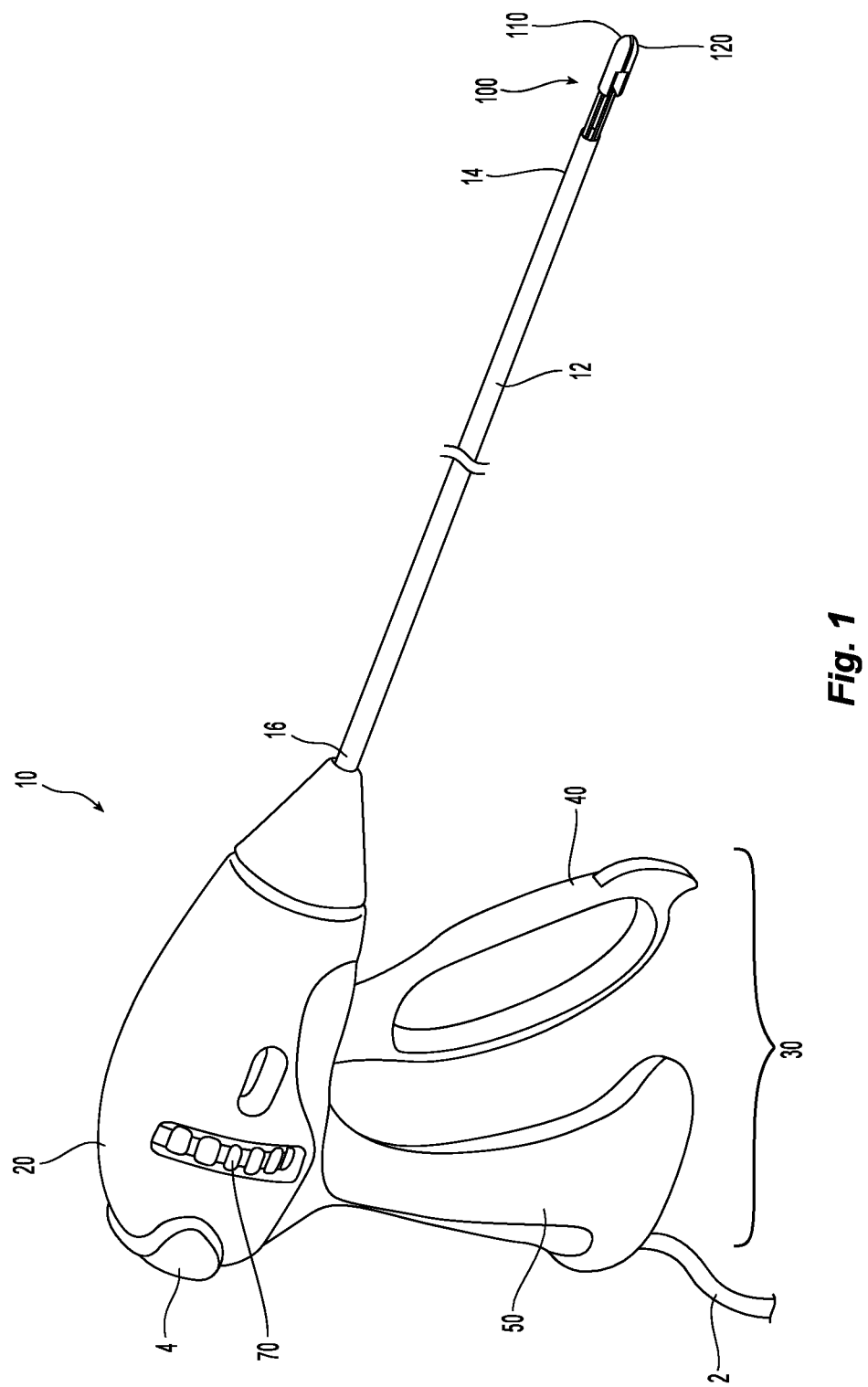
FIG. 1 is a perspective view of an endoscopic surgical forceps provided in accordance with the present disclosure.

Referring to FIG. 1, an embodiment of a surgical forceps provided in accordance with the present disclosure is shown generally identified by reference numeral 10. Although surgical forceps 10 is shown configured for use in connection with endoscopic surgical procedures, the aspects and features of surgical forceps 10 provided in accordance with the present disclosure are equally applicable for use in more traditional open surgical procedures and/or with any other suitable surgical instrument.

Forceps 10 generally includes a housing 20, a handle assembly 30, a rotating assembly 70, an activation switch 4, and an end effector assembly 100. Forceps 10 further includes a shaft 12 having a distal end 14 configured to engage end effector assembly 100 and a proximal end 16 that engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating surfaces 114, 124 of jaw members 110, 120, respectively. However, energy may be supplied to respective tissue-treating surfaces 114, 124 (FIG. 3) of jaw members 110, 120 in any other suitable fashion, e.g., via conductive structural components of forceps 10, brush-contacts, etc. Activation switch 4 is coupled between tissue-treating surfaces 114, 124 of jaw members 110, 120, respectively, and the source of energy for enabling the selective supply of energy to jaw members 110, 120 for treating tissue grasped therebetween. Rotating assembly 70 is rotatable in either direction to rotate end effector assembly 100 relative to housing 20.

Figure 2:
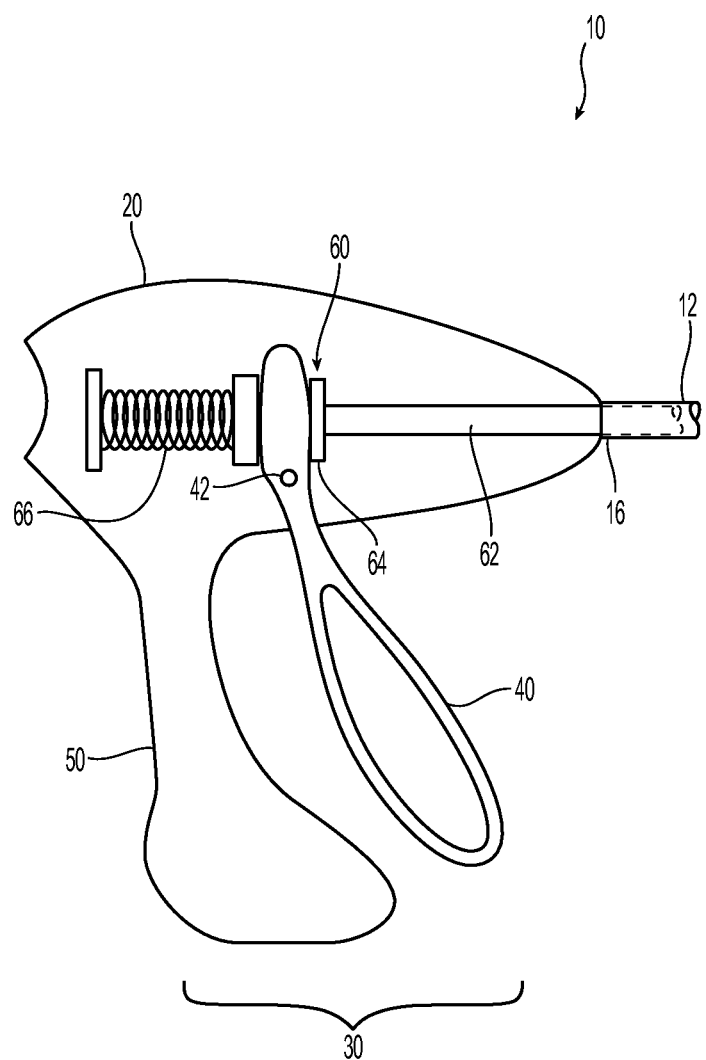
FIG. 2 is a side view of the proximal end of the forceps of FIG. 1, with a portion of the housing removed to enable illustration of the internal features thereof.

With additional reference to FIG. 2, handle assembly 30 includes a fixed handle 50 and a movable handle 40. Fixed handle 50 is integrally associated with housing 20 while movable handle 40 is pivotably coupled to housing 20 within housing 20 via a pivot 42. Movable handle 40 is also operably coupled to a drive assembly 60 operably associated with end effector assembly 100 that, together, mechanically cooperate to impart movement of jaw member 120 relative to jaw member 110 between an open position and a closed position for grasping tissue therebetween. More specifically, movable handle 40 is coupled to a drive bar 62 via a drive mandrel 64 such that movement of movable handle 40 relative to fixed handle 50 effects longitudinal translation of drive bar 62 through shaft 12 and relative to end effector assembly 100. As detailed below, the distal end of drive bar 62 supports jaw member 120 such that longitudinal translation of drive bar 62 through shaft 12 moves jaw member 120 relative to jaw member 110 between the open position (FIG. 3A) and the closed position (FIG. 3B).

As shown in FIGS. 1 and 2, movable handle 40 is initially spaced-apart from fixed handle 50 and, correspondingly, jaw members 110, 120 are disposed in the open position. Movable handle 40 is compressible from this initial position to a compressed position corresponding to the closed position of jaw members 110, 120. A biasing member 66 may be disposed about drive bar 62 and positioned to bias jaw members 110, 120 towards the open position and movable handle 40 apart from fixed handle 50. However, other configurations for biasing jaw members 110, 120 towards the spaced-apart position and/or positions of biasing member 66 for accomplishing the same are also contemplated.

Figure 3A:
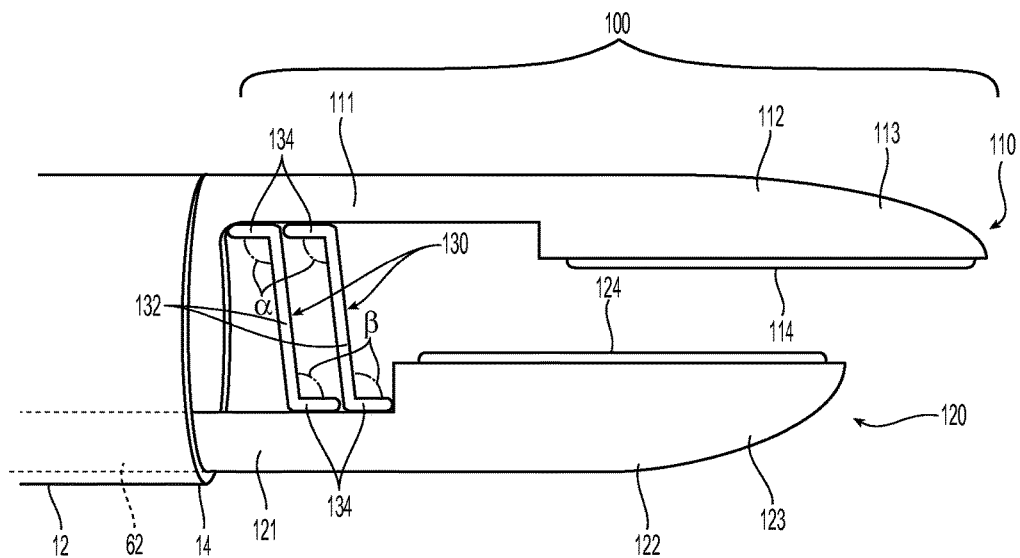
FIG. 3A is an enlarged, side, perspective view of the distal end of the forceps of FIG. 1, wherein jaw members of the end effector assembly of the forceps are disposed in an open position.
Figure 3B:
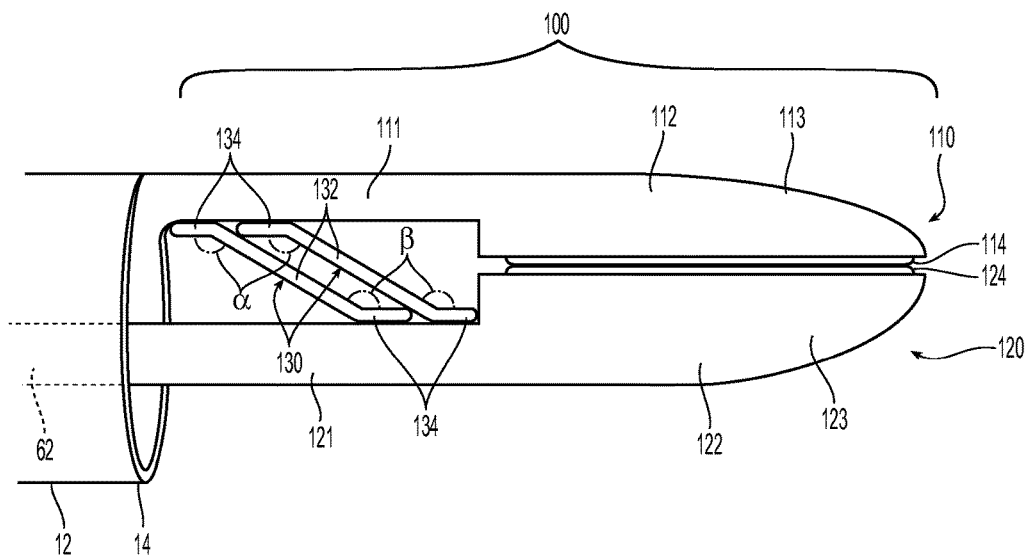
FIG. 3B is an enlarged, side, perspective view of the distal end of the forceps of FIG. 1, wherein the jaw members of the end effector assembly of the forceps are disposed in a closed position.

Referring to FIGS. 3A and 3B, in conjunction with FIGS. 1 and 2, end effector assembly 100 includes first and second jaw members 110, 120, each including a proximal flange 111, 121 and a distal jaw body 112, 122 including an outer insulative jaw housing 113, 123 and a tissue-treating surface 114, 124, respectively. Alternatively, one of both of jaw members 110, 12 may be monolithically formed from a conductive material. Proximal flange 111 of jaw member 110 is fixedly engaged with distal end 14 of shaft 12 and extends distally therefrom. Proximal flange 121 of jaw member 120 is supported on the distal end of drive bar 62, e.g., monolithically formed therewith or otherwise engaged thereto, and extends distally therefrom. A pair of resilient bands 130 extend between and operably interconnect proximal flanges 111, 121 of jaw members 110, 120, respectively, although it is also envisioned that greater or fewer bands 130 be provided. Bands 130 may define any suitable configuration and/or construction that serves to bias jaw members 110, 120 towards the open position (FIG. 3A), wherein jaw member 120 is proximally offset and spaced-apart from jaw member 110, and allows bands 130 to flex in response to distal translation of drive bar 62 such that jaw member 120 is moved distally into alignment with jaw member 110 and towards jaw member 110 into approximation therewith to achieve the closed position (FIG. 3B).

Each band 130 may be formed from spring steel and define a body portion 132 and a leg 134 at each end of body portion 132. Legs 134 of each band 130 are engaged to proximal flanges 111, 121 of jaw members 110, 120, e.g., via adhesion, bolting, welding, or other suitable engagement, and are disposed in generally parallel orientation relative to one another. Body portions 132 of bands 130 extend between proximal flanges 111, 121 of jaw members 110, 120 and are also disposed in generally parallel orientation relative to one another. Body portions 132 are disposed in transverse orientation relative to legs 134.

In the open position of jaw members 110, 120 (FIG. 3A), the interior angles "α," "β" defined at the living hinges between body portions 132 and the legs 134 engaged with respective proximal flanges 111, 121 are at a minimum. Upon distal translation of drive bar 62, e.g., via actuation of movable handle 40 (FIGS. 1 and 2), jaw member 120 is urged distally relative to jaw member 110. In order to accommodate this distal movement, the living hinges defined between body portions 132 and the legs 134 engaged with respective proximal flanges 111, 121 are flexed so as to increase angles "α," "β," respectively, to a maximum, thereby urging jaw member 120 towards jaw member 110 as jaw member 120 is moved distally. Ultimately, the closed position (FIG. 3B) of jaw members 110, 120 is reached, wherein jaw member 120 is aligned with and approximated relative to jaw member 110. Jaw members 110, 120 may be moved to the closed position to grasp tissue between tissue-treating surfaces 114, 124. Thereafter, energy may be supplied to tissue-treating surface 114 of jaw member 110 and/or tissue-treating surface 124 of jaw member 120 to treat tissue grasped therebetween. As a result of the resilient configuration of the spring steel bands 130, jaw member 120 is returned proximally and apart from jaw member 110 upon release or return of movable handle 40 (FIGS. 1 and 2) to its initial position, e.g., to release treated tissue.

Turning now to FIGS. 4A and 4B, the distal end of another embodiment of a forceps 10' provided in accordance with the present disclosure is shown generally including a shaft 12' and an end effector assembly 200 disposed at distal end 14' of shaft 12'. The proximal end of forceps 10' may include components similar to those detailed above with respect to forceps 10 (FIG. 1), e.g., a handle assembly and drive assembly for selectively translating drive bar 62' through shaft 12' to move jaw members 210, 220 of end effector assembly 200 between open and closed positions, as detailed below.

End effector assembly 200 includes first and second jaw members 210, 220, each including a proximal flange 211, 221 and a distal jaw body 212, 222 including an outer insulative jaw housing 213, 223 and a tissue-treating surface 214, 224, respectively. Proximal flange 211 of jaw member 210 is fixedly engaged with distal end 14' of shaft 12' and extends distally therefrom. A nut 226 is fixedly engaged, e.g., monolithically formed or otherwise engaged, with proximal flange 221 of jaw member 220 at the proximal end thereof. Nut 226 defines an interior threaded bore 227 and includes an annular recess 229 defined about the exterior thereof. Nut 226 operably receives a lead screw 68 at least partially within threaded bore 227 thereof. Lead screw 68 is translationally and rotationally fixed relative to shaft 12' and includes drive bar 62' slidably disposed thereabout. Drive bar 62' includes an inwardly-extending radial lip 69 that is received within annular recess 229 of nut 226 so as to rotatably engage jaw member 220 with drive bar 62'. More specifically, as a result of this configuration, distal translation of drive bar 62' about lead screw 68 urges nut 226 and, thus, jaw member 220 distally relative to shaft 12' and jaw member 210, while the operable engagement of nut 226 about lead screw 68 urges nut 226 to rotate relative to lead screw 68 upon such distal translation, thereby rotating jaw member 220 relative to shaft 12' and jaw member 210. As can be appreciated, jaw member 220 is rotated relative to shaft 12' about an axis parallel to or coaxial with the longitudinal axis of shaft 12'. However, other configurations are also contemplated.

In the open position of end effector assembly 200 (FIG. 4A), jaw member 220 is longitudinally offset, rotationally offset, and spaced-apart relative to jaw member 210. Upon distal translation of drive bar 62', drive bar 62' urges jaw member 220 distally into longitudinal alignment with jaw member 210 while the operable engagement of nut 226 about lead screw 68 urges jaw member 220 to rotate into rotational alignment and approximation relative to jaw member 210, thus achieving the closed position of jaw members 210, 220 (FIG. 4B). Jaw members 210, 220 may be moved to the closed position to grasp tissue between tissue-treating surfaces 214, 224. Thereafter, energy may be supplied to tissue-treating surface 214 of jaw member 210 and/or tissue-treating surface 224 of jaw member 220 to treat tissue grasped therebetween. Proximal translation of drive bar 62' pulls jaw member 220 proximally relative to jaw member 210, while the operable engagement of nut 226 about lead screw 68 urges jaw member 220 to rotate away from and out of rotational alignment with jaw member 210, thus returning jaw members 210, 220 to the open position.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly, including:
   first and second jaw members, each of the first and second jaw members including a proximal flange and a distal jaw body defining a tissue-treating surface, the second jaw member proximally offset and spaced-apart from the first jaw member when in a first, open position; and
   at least one resilient band defining first and second interior angles and extending between and interconnecting the proximal flanges of the first and second jaw members, the at least one resilient band configured to bias the first and second jaw members towards the first, open position and
   a drive bar, wherein a distal portion of the drive bar directly supports the proximal flange of the second jaw member, and wherein distal translation of the drive bar effectuates a corresponding distal translation of the second jaw member relative to the first jaw member, the at least one resilient band configured to flex in response to the distal translation of the second jaw member and move the second jaw member into a second, approximated position where the first and second jaw members are longitudinally aligned.

2. The forceps according to claim 1, wherein the at least one resilient band includes at least one spring steel band.

3. The forceps according to claim 1, wherein the at least one resilient band includes first and second legs engaged with the respective proximal flanges of the first and second jaw members and a body interconnecting the first and second legs.

4. The forceps according to claim 3, wherein, in the first, open position, the first and second interior angles are at a minimum and wherein, in the second, approximated position, the first and second interior angles are at a maximum.

5. The forceps according to claim 1, further including:
   a shaft having the proximal flange of the first jaw member engaged thereto
   wherein the drive bar is slidably disposed within the shaft, the drive bar including the proximal flange of the second jaw member engaged thereto.

6. The forceps according to claim 5, wherein distal translation of the drive bar through and relative to the shaft moves the second jaw member from the first, open position to the second, approximated position to grasp tissue between the tissue-treating surfaces of the first and second jaw members.

7. The forceps according to claim 5, further including a handle assembly operably associated with the drive bar, the handle assembly including a movable handle selectively actuatable for translating the drive bar through and relative to the shaft.

8. The forceps according to claim 1, wherein at least one of the tissue-treating surfaces is adapted to connect to a source of energy for treating tissue grasped between the tissue-treating surfaces of the first and second jaw members.

* * * * *